United States Patent
Bayless et al.

(10) Patent No.: US 11,324,702 B2
(45) Date of Patent: May 10, 2022

(54) SOFT GEL COMPOSITIONS AND CAPSULES MADE FROM THE SAME

(71) Applicant: Captek Softgel International, Inc., Cerritos, CA (US)

(72) Inventors: Ronnie E. Bayless, Norwalk, CA (US); Timothy Brian Chiprich, Huntington Beach, CA (US)

(73) Assignee: Captek Softgel International, Inc., Cerritos, CA (US)

( * ) Notice: Subject to any disclaimer, the term of this patent is extended or adjusted under 35 U.S.C. 154(b) by 183 days.

(21) Appl. No.: 16/289,416

(22) Filed: Feb. 28, 2019

(65) Prior Publication Data

US 2019/0269623 A1    Sep. 5, 2019

Related U.S. Application Data

(60) Provisional application No. 62/637,547, filed on Mar. 2, 2018.

(51) Int. Cl.
- *A61K 9/50* (2006.01)
- *A61K 9/48* (2006.01)
- *A61K 47/36* (2006.01)

(52) U.S. Cl.
CPC .......... *A61K 9/5015* (2013.01); *A61K 9/4816* (2013.01); *A61K 9/5036* (2013.01); *A61K 9/5063* (2013.01); *A61K 9/5089* (2013.01); *A61K 47/36* (2013.01)

(58) Field of Classification Search
CPC .. A61K 9/5015; A61K 9/5089; A61K 9/5036; A61K 9/5063; A61K 9/4816; A61K 47/36
See application file for complete search history.

(56) References Cited

U.S. PATENT DOCUMENTS

| | | | |
|---|---|---|---|
| 2003/0161872 A1* | 8/2003 | Chen | A61K 9/4816 424/452 |
| 2007/0292501 A1* | 12/2007 | Udell | A61K 9/0056 424/456 |
| 2013/0302309 A1 | 11/2013 | Yang | |
| 2015/0297528 A1 | 10/2015 | Shuai et al. | |

FOREIGN PATENT DOCUMENTS

| | | | |
|---|---|---|---|
| EP | 1598062 A1 | | 11/2005 |
| EP | 1925298 | * | 5/2008 |
| WO | 0191721 A2 | | 12/2001 |

OTHER PUBLICATIONS

"Seamless Soft Capsules Which Easily Disintegrate in Gastric Juice—Comprise Agar and Water-Soluble Polymer, Partic. With Added Plasticiser", Wpi Derwent, 2003, 2 pages.

PCT/US2019/020144, "International Search Report and Written Opinion", dated Jun. 12, 2019, 11 pages.

\* cited by examiner

*Primary Examiner* — Shirley V Gembeh
(74) *Attorney, Agent, or Firm* — FisherBroyles, LLP

(57) ABSTRACT

The present disclosure generally relates to film-forming compositions and capsules formed from such compositions, including processes for using such compositions to make capsules. In some embodiments, the film-forming compositions are free of animal products and carrageenan.

4 Claims, 1 Drawing Sheet

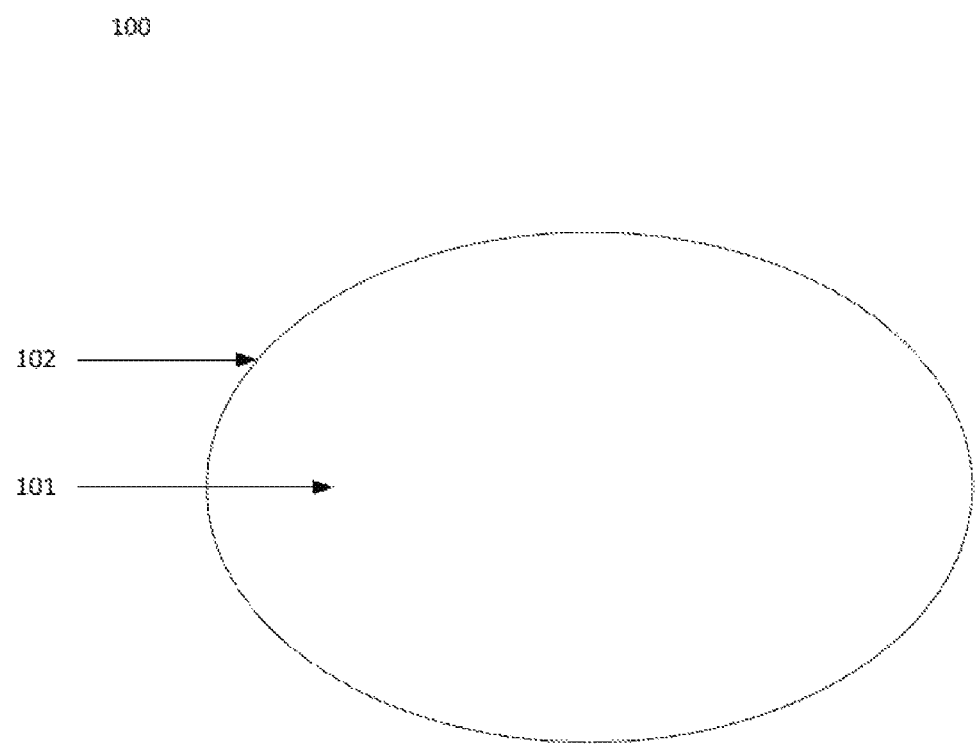

SOFT GEL COMPOSITIONS AND CAPSULES MADE FROM THE SAME

TECHNICAL FIELD

The present disclosure generally relates to film-forming compositions and capsules formed from such compositions, including processes for using such compositions to make capsules. In some embodiments, the film-forming compositions are free of animal products and carrageenan.

BACKGROUND

Soft gel capsules provide a useful means of packaging and delivering various compounds, including nutritional supplements and various drug compounds. Gelatin has been commonly used to make the films that encapsulate such active ingredients. Gelatin is a hydrolyzed protein obtained from heating animal bones or cartilage under heat and pressure in the presence of water. But the use of gelatin suffers from certain drawbacks. For example, some people may object to consuming products made from ingredients of animal origin, either for ethical or religious reasons. And, because of its animal origins, there is some risk that gelatin may carry prions of certain animal-borne diseases.

Significant efforts have been made in developing replacements for gelatin in making soft gel capsules. Such compositions often use carrageenans, which are linear sulfated polysaccharides extracted from red algae. And while such carrageenan-based films provide a suitable replacement for gelatin-based films, concerns have arisen over inflammation-related side-effects that some people may experience in connection with ingesting carrageenans.

Therefore, there is a need to continue developing film-forming compositions that are suitable for use in making soft gel capsules and that do not require the use of gelatin or carrageenans.

SUMMARY

The compositions disclosed herein provide an improved material that are suitable for use in encapsulating soft gel capsules and that do not necessarily require the inclusion of gelatin or carrageenans. In many embodiments, the resulting capsules show suitably low cracking during packaging and do not stick together to any substantial degree during storage.

In a first aspect, the disclosure provides film-forming compositions, the compositions comprising: (a) from 1 to 60 percent by weight of a hydroxyalkylated plant starch, a plant sugar, or a combination thereof; (b) from 1 to 30 percent by weight agar; and (c) from 30 to 80 percent by weight water; wherein the percents by weight are based on the total weight of the film-forming compositions.

In a second aspect, the disclosure provides soft capsules, comprising: (a) a fill material; and (b) an outer shell encapsulating the fill material, wherein the outer shell is formed by encapsulating the fill material with the film-forming composition of the first aspect (or any embodiments thereof).

In a third aspect, the disclosure provides methods of forming a soft capsule, the methods comprising: (a) providing the film-forming composition of the first aspect (or any embodiments thereof) and a fill material; and (b) encapsulating the fill material within the film-forming composition to form a sealed capsule.

In a fourth aspect, the disclosure provides soft capsules, comprising: (a) a fill material; and (b) an outer shell encapsulating the fill material, wherein the outer shell comprises: (i) from 1 to 80 percent by weight of a hydroxyalkylated plant starch, a plant sugar, or a combination thereof; and (ii) from 1 to 60 percent by weight agar; wherein the percents by weight are based on the total weight of the outer shell.

Further aspects and embodiments of the disclosure are set forth in the following drawings, detailed description, and claims.

BRIEF DESCRIPTION OF DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

FIG. 1 shows an illustrative embodiment of a soft gel capsule disclosed herein.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "introduce" or "introduction" refers to any disposition of a substance of a mixture of substances with another substance or mixture of substances to form a new mixture of substances. In some instances, the introduction can result in a chemical reaction occurring, such that new covalent interactions are formed between atoms. In other instances, however, the introduction does not result in a chemical reaction occurring. In some such instances, non-covalent interactions may form between certain substances.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the term "provide" or "providing" is to be given its broadest reasonable interpretation, and does not imply that items are provided in a particular way or manner. For example, a technician who arranges certain items for use in conducting a test or experiment is engaged in the act of providing. Moreover, when providing two or more items, the two or more items need not be part of a common package or kit or from a common source.

As used herein, "carrageenan" or "carrageenans" refers to one or more members of a family of linear sulfated polysaccharides derived from red algae, and any salts thereof, including, but not limited to, alpha-carrageenan, beta-carrageenan, gamma-carrageenan, delta-carrageenan, kappa-carrageenan, mu-carrageenan, nu-carrageenan, iota-carrageenan, lambda-carrageenan, theta-carrageenan, and any salts thereof. Carrageenan compositions usually have a weight-average molecular weight ranging from 200,000 to 800,000 Da, as determined by gel permeation chromatography.

As used herein, "agar" refers to one or more members of a family of compounds derived from polysaccharide agarose, which forms the cell walls of algae called agarophytes. In most instances, agar includes a mixture of two polysaccharides: agarose and agaropectin, with agarose making up a higher proportion of the mixture. Agarose is a linear polymer, made up of repeating units of agarobiose, a disaccharide made up of D-galactose and 3,6-anhydro-L-galactopyranose. Agaropectin is a heterogeneous mixture of smaller molecules that occur in lesser amounts, and is made up of alternating units of D-galactose and L-galactose heavily modified with acidic side-groups, such as sulfate and pyruvate.

Other terms are defined in other portions of this description, even though not included in this subsection.

Film-Forming Compositions

In at least one aspect, the disclosure provides film-forming compositions, the compositions comprising: (a) from 1 to 60 percent by weight of a hydroxyalkylated plant starch, a plant sugar, or a combination thereof; (b) from 1 to 30 percent by weight agar; and (c) from 30 to 80 percent by weight water; wherein the percents by weight are based on the total weight of the film-forming compositions.

The film-forming compositions disclosed herein include hydroxyalkylated plant starch. Any suitable kind of hydroxyalkylated plant starch can be used. In some embodiments, the hydroxyalkylated plant starch is a hydroxymethylated plant starch, a hydroxyethylated plant starch, a hydroxypropylated plant starch, or some combination thereof. Moreover, the plant starch can be derived from any suitable plant. For example, in some embodiments, the hydroxyalkylated plant starch is a hydroxyethylated plant starch, which is a hydroxyethylated starch of plants selected from the group consisting of: beans (including favas, lentils, mung beans, peas, and chickpeas), wheat, potatoes, cassava, tapioca, corn, soybeans, peas, rice, acorns, arrowroot, arracacha, bananas, barley, breadfruit, buckwheat, canna, colacasia, katakuri, kudzu, malanga, millet, oats, oca, polynesian arrowroot, sago, sorghum, sweet potatoes, rye, taro, chestnuts, water chestnuts and yams, and any combinations thereof. In some other embodiments, the hydroxyalkylated plant starch is a hydroxypropylated plant starch, which is a hydroxypropylated starch of plants selected from the group consisting of: beans (including favas, lentils, mung beans, peas, and chickpeas), wheat, potatoes, cassava, tapioca, corn, soybeans, peas, rice, acorns, arrowroot, arracacha, bananas, barley, breadfruit, buckwheat, canna, colacasia, katakuri, kudzu, malanga, millet, oats, oca, polynesian arrowroot, sago, sorghum, sweet potatoes, rye, taro, chestnuts, water chestnuts and yams, and any combinations thereof. In some embodiments, the hydroxyalkylated plant starch is a hydroxyalkylated tapioca starch, such as those described in U.S. Patent Application Publication No. 2015/0297528, which is incorporated herein by reference. In some further embodiments, the hydroxyalkylated plant starch is a hydroxyethylated tapioca starch or a hydroxypropylated tapioca starch. In some further such embodiments, the hydroxyalkylated plant starch is a hydroxypropylated tapioca starch.

The aforementioned hydroxyalkylated plant starch according to any of the embodiments set forth above, can make up any suitable proportion of the film-forming composition. For example, in some embodiments, the hydroxyalkylated plant starch makes up from 1 to 30 percent by weight, or from 1 to 20 percent by weight, or from 1 to 10 percent by weight, or from 1 to 7 percent by weight, or from 2 to 7 percent by weight, or from 2 to 6 percent by weight, or from 3 to 5 percent by weight, of the film-forming composition, based on the total weight of the film-forming composition. In some embodiments, the hydroxyalkylated plant starch makes up about 1.0 percent by weight, or about 2.0 percent by weight, or about 3.0 percent by weight, or about 4.0 percent by weight, or about 5.0 percent by weight, or about 6.0 percent by weight, or about 7.0 percent by weight, or about 8.0 percent by weight, or about 9.0 percent by weight, or about 10.0 percent by weight, of the film-forming composition, based on the total weight of the film-forming composition.

In some embodiments, the film-forming compositions disclosed herein also comprise one or more sugars, such as a plant sugar. Any suitable plant sugars can be used, such as a pentose, a hexose, or any dimers thereof, with either L or D enantiomers of the sugar being suitable. In some further embodiments, the plant sugar is a hexose, which is selected from the group consisting of: allose, altrose, glucose, mannose, gulose, idose, galactose, talose, psicose, fructose, sorbose, tagatose, any dimers of the foregoing, and any combinations thereof. In some embodiments, the plant sugar is a dextrose, such as tapioca dextrose.

The aforementioned plant sugar according to any of the embodiments set forth above, can make up any suitable proportion of the film-forming composition. For example, in some embodiments, the plant sugar makes up from 1 to 60 percent by weight, or from 1 to 30 percent by weight, or from 1 to 20 percent by weight, or from 1 to 10 percent by weight, or from 1 to 7 percent by weight, or from 2 to 7 percent by weight, or from 2 to 6 percent by weight, or from 3 to 5 percent by weight, of the film-forming composition, based on the total weight of the film-forming composition. In some embodiments, the plant sugar makes up about 1.0 percent by weight, or about 2.0 percent by weight, or about 3.0 percent by weight, or about 4.0 percent by weight, or about 5.0 percent by weight, or about 6.0 percent by weight, or about 7.0 percent by weight, or about 8.0 percent by weight, or about 9.0 percent by weight, or about 10.0 percent by weight, of the film-forming composition, based on the total weight of the film-forming composition.

In some examples, the total amount of hydroxyalkylated plant starch and plant sugar makes up from 1 to 60 percent by weight, or from 1 to 30 percent by weight, or from 1 to 20 percent by weight, or from 1 to 10 percent by weight, or from 1 to 7 percent by weight, or from 2 to 7 percent by weight, or from 2 to 6 percent by weight, or from 3 to 5 percent by weight, of the film-forming composition, based on the total weight of the film-forming composition.

In some embodiments, the film-forming compositions can include suitable amounts of plasticizers. Any suitable plasticizer or combination of plasticizers can be used, including, but not limited to low-molecular-weight polyols, sugar alcohols, and the like. Low-molecular weight polyols have a molecular weight of less than about 200 g/mol.

Thus, in some embodiments, the film-forming compositions include one or more low-molecular-weight polyols, e.g., polyols having from 2 to 6, or from 2 to 5, or from 2 to 4 carbon atoms. Non-limiting examples of low-molecular-weight polyols include, but are not limited to ethylene glycol, 1,3-propylene glycol, 1,2-propylene glycol, glycerin, glycerol, or combinations thereof. Such polyols can be included in any suitable amount. For example, in some embodiments, the film-forming compositions include from 1 to 15 percent by weight, or from 3 to 15 percent by weight, or from 5 to 15 percent by weight, or from 6 to 12 percent by weight, or from 7 to 11 percent by weight, or from 6 to 10 percent by weight, of low-molecular-weight polyols.

And, in some embodiments, the film-forming compositions include one or more sugar alcohols. Any suitable sugar alcohol can be used, including, but not limited to maltitol, sorbitol, xylitol, erythritol, isomalt, or combinations thereof. Such sugar alcohols can be included in the film-forming compositions in any suitable amount. For example, in some embodiments, the film-forming compositions include from 1 to 15 percent by weight, or from 3 to 15 percent by weight, or from 5 to 15 percent by weight, or from 5 to 10 percent by weight, or from 3 to 10 percent by weight, or from 3 to 15 percent by weight, of sugar alcohols.

In some embodiments, the film-forming compositions can include plant starch. Examples of plant starch include, but are not limited to, a starch from plants selected from the group consisting of: beans (including favas, lentils, mung beans, peas, and chickpeas), wheat, potatoes, cassava, tapioca, corn, soybeans, peas, rice, acorns, arrowroot, arracacha, bananas, barley, breadfruit, buckwheat, canna, colacasia, katakuri, kudzu, malanga, millet, oats, oca, polynesian arrowroot, sago, sorghum, sweet potatoes, rye, taro, chestnuts, water chestnuts and yams, and any combinations thereof.

In some embodiments, the film-forming composition includes one or more phosphoglycerides. Non-limiting examples of such phosphoglycerides include lecithin.

In some embodiments, the film-forming compositions include one or more additives, such as surfactants, colorants, pigments, flavoring agents, stabilizers, preservatives, buffers, polymer ingredients (e.g., pullulan, furcelleran, etc.), and the like.

In some embodiments, the film-forming composition comprises from 2 to 7 percent by weight of a hydroxyalkylated plant starch, from 2 to 7 percent by weight of a plant sugar, from 15 to 25 percent by weight of agar, from 5 to 10 percent by weight of a polyol, and from about 2 to 12 percent by weight of a sugar alcohol, based on the total weight of the composition. In some embodiments, the film-forming composition comprises from 2 to 7 percent by weight of a modified tapioca starch, from 2 to 7 percent by weight of a tapioca dextrose, from 15 to 25 percent by weight of agar, from 5 to 10 percent by weight of glycerol, and from about 2 to 12 percent by weight of a sorbitol, based on the total weight of the composition.

In some embodiments, it may be desirable that the film-forming composition be free or substantially free of products derived from animals. Thus, in some embodiments, the composition comprises no more than 5 percent by weight, or no more than 3 percent by weight, or no more than 1 percent by weight, or no more than 0.5 percent by weight, or no more than 0.2 percent by weight, of products derived from animals, based on the total weight of the composition.

In some embodiments, it may be desirable that the film-forming composition be free or substantially free of carrageenan. Thus, in some embodiments, the composition comprises no more than 1 percent by weight, or no more than 0.5 percent by weight, or no more than 0.2 percent by weight, or no more than 0.1 percent by weight, of carrageenan, based on the total weight of the composition.

Methods of Forming Capsules

The film-forming compositions disclosed above can be useful for forming an encapsulant for a soft-gel capsule. Thus in one or more aspects, the disclosure provides methods of forming a soft capsule, the methods comprising: (a) providing the film-forming composition according to any of the embodiments disclosed above, and a fill material; and (b) encapsulating the fill material within the film-forming composition to form a sealed capsule.

Any suitable fill materials can be used. For example, in some embodiments, the fill material is an oil, a hydrophilic liquid, or an emulsion. Various hydrophobic or hydrophilic active agents can be included within such oils, hydrophilic liquids, or emulsions. Suitable fill materials include, but are not limited to, foods, food extracts, vitamins, minerals, supplements, nutraceuticals, pharmaceuticals, and the like.

The encapsulating can be carried out by any suitable process, such as those set forth in the relevant literature. In some embodiments, the encapsulating is carried out by a rotary die process, followed by drying. In some embodiments, the resulting encapsulant has a shell thickness ranging from 0.01 cm to 0.25 cm. In some examples, encapsulation machines may be equipped with high volume blowers for the outside of the ribbons to aid in water removal. In some examples, encapsulation dies may require a deeper outer pocket design to accommodate thicker than normal shell material ribbons. In some cases, standard rotary die encapsulation machines may use additional modifications to accommodate the specific properties of the formulation. Modifications may include but are not limited to die roll heaters, die cooling air, ribbon heaters, capsule cooling air, modified tumble dryers, or capsule cooling liquid baths Soft-Gel Capsules The processes described above can be used to make soft-gel capsules. In at least one aspect, the disclosure provides soft capsules, comprising: (a) a fill material; and (b) an outer shell encapsulating the fill material, wherein the outer shell is formed by encapsulating the fill material with the film-forming composition described according to any of the embodiments set forth above.

In at least another aspect, the disclosure provides soft capsules, comprising: (a) a fill material; and (b) an outer shell encapsulating the fill material, wherein the outer shell comprises: (i) from 1 to 80 percent by weight of a hydroxyalkylated plant starch, a plant sugar, or a combination thereof; and (ii) from 1 to 60 percent by weight agar; wherein the percents by weight are based on the total weight of the outer shell.

The compositional makeup of the outer shell for such aspects are similar to those for the film-forming compositions described above, except that amounts for the non-water ingredients is higher due to evaporation of water during the encapsulating process and subsequent drying steps. Thus, the various embodiments set forth for the ingredients of the film-forming compositions also apply with respect to the outer shell, except that different weight percents for the ingredients may apply.

In some embodiments, the outer shell comprises from 1 to 60 percent by weight, or from 1 to 50 percent by weight, or from 1 to 40 percent by weight, or from 1 to 30 percent by weight, of a hydroxyalkylated plant starch (according to any of the embodiments set forth above), based on the total weight of the composition.

In some embodiments, the outer shell comprises from 1 to 50 percent by weight, or from 1 to 40 percent by weight, or from 1 to 30 percent by weight, or from 1 to 20 percent by weight, of a plant sugar (according to any of the embodiments set forth above), based on the total weight of the composition.

In some embodiments, the outer shell can include suitable amounts of plasticizers. Any suitable plasticizer or combination of plasticizers can be used, including, but not limited to low-molecular-weight polyols, sugar alcohols, and the like.

Thus, in some embodiments, the outer shell further comprises from 1 to 20 percent by weight, or from 3 to 20 percent by weight, or from 5 to 20 percent by weight, of low-molecular-weight polyols (according to any of the embodiments set forth above).

And, in some embodiments, the outer shell further comprises from 1 to 20 percent by weight, or from 3 to 20 percent by weight, or from 5 to 20 percent by weight, of sugar alcohols (according to any of the embodiments set forth above).

In some embodiments, the outer shell comprises no more than 5 percent by weight, or no more than 3 percent by weight, or no more than 1 percent by weight, or no more than 0.5 percent by weight, or no more than 0.2 percent by weight, of products derived from animals, based on the total weight of the composition.

In some embodiments, the outer shell comprises no more than 1 percent by weight, or no more than 0.5 percent by weight, or no more than 0.2 percent by weight, or no more than 0.1 percent by weight, of carrageenan, based on the total weight of the composition.

FIG. 1 shows a drawing of a soft gel capsule 100 of certain embodiments disclosed herein. The soft gel capsule comprises an inner portion 101 that includes a fill material, and which is encapsulated by an outer shell 102.

EXAMPLES

Example 1—Film-Forming Compositions

A film-forming composition having the composition set forth in Table 1 was made, wherein the ingredients were mixed together by standard means.

TABLE 1

| Ingredient | Amount (weight percent) |
| --- | --- |
| Modified tapioca starch | 2.2 |
| Tapioca dextrose | 2.2 |
| Agar | 17.8 |
| Glycerol | 8.9 |
| Anhydrous sorbitol (76% solution) | 8.9 |
| Water | remainder |

TABLE 2

| Ingredient | Amount (weight percent) |
| --- | --- |
| Modified tapioca starch | 4.9 |
| Tapioca dextrose | 4.9 |
| Agar | 19.8 |
| Glycerol | 7.3 |
| Anhydrous sorbitol (76% solution) | 3.1 |
| Water | remainder |

Example 2—Performance Testing

Soft-gel capsules were formed and dried using conventional techniques using the film-forming composition of Example 1, Table 1, which was compared to soft-gel capsules formed from compositions formed from animal gelatin, FMC Marine Gel (containing carrageenan), and modified tapioca starch (Er-Kang). The soft-gel shell materials of each type were tested for puncture strength, deformation at break, and capsule burst strength. Results are shown in Table 3. The puncture strength uses a dried film of the test polymer and measures the minimum force, when applied to a stylus at a constant strain rate, that is necessary to puncture the film. The deformation at break measures the minimum distance of deformation that is necessary to cause the film to break. The capsule burst strength measures the minimum force, when applied via a flat surface at a constant strain rate, that is necessary to rupture the dried capsule. The film puncture test and capsule burst test use an Instron, Texture Analyzer, or similar testing machine in compression mode.

TABLE 3

|  | Puncture Strength (gm) | Deformation at Break (mm) | Capsule Burst Strength (kg) |
|---|---|---|---|
| Example 1 | 60,664 | 8.8 | 51 |
| Animal Gelatin | 36,000 | 13.0 | 40-50 |
| FMC Marine Gel | 30,000 | 8.4 | 25 |
| Mod. Tapioca Starch (Er-Kang) | 47,000 | 12.3 | 30-45 |

The invention claimed is:

1. A soft capsule, comprising:
(a) a fill material; and
(b) an outer shell encapsulating the fill material, wherein the outer shell is formed by encapsulating the fill material with the film-forming composition comprising
(i) from 0 to 10 percent by weight of a hydroxyalkylated plant starch, and from 0 to 60 percent by weight of a plant sugar, wherein the film forming composition comprises from 1 to 60 percent by weight of a combination of the hydroxyalkylated plant starch and the plant sugar;
(ii) from 1 to 30 percent by weight agar; and
(iii) from 30 to 80 percent by weight water;
wherein the percents by weight are based on the total weight of the film-forming composition.

2. A method of forming a soft capsule, the method comprising:
(a) providing the film-forming composition of claim 1 and the fill material of claim 1; and
(b) encapsulating the fill material within the film-forming composition to form a sealed capsule.

3. The soft capsule of claim 1, wherein the film-forming composition comprises no more than 0.5 percent by weight carrageenan.

4. The soft capsule of claim 1, wherein the film forming composition comprises at least 15 percent by weight agar.

* * * * *